(12) United States Patent
Edvardsson

(10) Patent No.: US 8,182,736 B2
(45) Date of Patent: *May 22, 2012

(54) APPARATUS AND METHOD FOR FORMING AIR-LAID ABSORBENT CORES

(75) Inventor: Gunnar Edvardsson, Bohus Björkö (SE)

(73) Assignee: SCA Hygiene Products AB, Gothenburg (SE)

( * ) Notice: Subject to any disclaimer, the term of this patent is extended or adjusted under 35 U.S.C. 154(b) by 172 days.

This patent is subject to a terminal disclaimer.

(21) Appl. No.: 12/373,780

(22) PCT Filed: Jul. 20, 2006

(86) PCT No.: PCT/SE2006/050269
§ 371 (c)(1),
(2), (4) Date: Jan. 14, 2009

(87) PCT Pub. No.: WO2008/010754
PCT Pub. Date: Jan. 24, 2008

(65) Prior Publication Data
US 2009/0255621 A1    Oct. 15, 2009

(51) Int. Cl.
*B27N 3/08* (2006.01)

(52) U.S. Cl. ........ 264/517; 264/299; 264/310; 264/319; 425/436 R

(58) Field of Classification Search .......... None
See application file for complete search history.

(56) References Cited

U.S. PATENT DOCUMENTS

| | | | |
|---|---|---|---|
| 3,973,291 A | 8/1976 | Kolbach | |
| 4,388,056 A | 6/1983 | Lee et al. | |
| 4,598,441 A | 7/1986 | Stemmler | |
| 5,030,314 A | 7/1991 | Lang | |
| 5,575,874 A | 11/1996 | Griesbach, III et al. | |
| 6,330,735 B1 | 12/2001 | Hahn et al. | |
| 6,652,798 B1 | 11/2003 | Edvardsson | |

(Continued)

FOREIGN PATENT DOCUMENTS

DE    1 510 427 B    10/1970

(Continued)

OTHER PUBLICATIONS

U.S. Appl. No. 12/373,786, Edvardsson et al., "An Apparatus and Method for Forming Air-Laid Absorbent Cores", filed Jan. 14, 2009.

(Continued)

*Primary Examiner* — Monica A Huson

(74) *Attorney, Agent, or Firm* — Buchanan Ingersoll & Rooney PC

(57) ABSTRACT

An apparatus for forming air-laid absorbent cores, having a first and second mat-forming wheel. Means are also provided for applying a first and second web of casing material onto the peripheral surface of the first and second mat-forming wheel, respectively, for providing a third web of casing material into the nip between the first and second mat-forming wheel, for applying an adhesive coating on both sides of the third web, the mat-forming wheels being so positioned that the formed core elements on the respective first and second mat-forming wheels will abut the third web when passing the nip between the first and second mat-forming wheel, and for pressing together the portions of the three webs located outside the contour of the core element, containing the first and second core element, whereby the air-laid core elements will encapsulated in casing material. Also, a method for forming air-laid absorbent cores.

16 Claims, 2 Drawing Sheets

U.S. PATENT DOCUMENTS

| | | |
|---|---|---|
| 6,811,642 B2 | 11/2004 | Ochi |
| 2002/0056516 A1 | 5/2002 | Ochi |
| 2005/0109442 A1 | 5/2005 | Neubauer et al. |
| 2006/0021695 A1 | 2/2006 | Blessing et al. |
| 2006/0024433 A1 | 2/2006 | Blessing et al. |
| 2006/0048880 A1 | 3/2006 | Blessing et al. |

FOREIGN PATENT DOCUMENTS

| | | |
|---|---|---|
| DE | 43 35 919 A1 | 4/1995 |
| EP | 0 292 624 A1 | 11/1988 |
| EP | 0 958 801 B1 | 11/1999 |
| EP | 1 082 081 B1 | 3/2001 |
| EP | 1 621 167 A2 | 2/2006 |
| FR | 2 690 843 A1 | 11/1993 |
| JP | 61-28003 A | 2/1986 |
| JP | 7-150456 A | 6/1995 |
| JP | 11-318977 A | 11/1999 |
| WO | WO 99/60964 A1 | 12/1999 |
| WO | WO 2005/072671 A1 | 8/2005 |

OTHER PUBLICATIONS

U.S. Appl. No. 12/373,728, Edvardsson et al., "Mat-Forming Wheel", filed Jan. 14, 2009.

U.S. Appl. No. 12/373,729, Edvardsson, "An Apparatus and Method for Forming Air-Laid Absorbent Cores", filed Jan. 14, 2009.

English language translation of an Official Action issued on Nov. 1, 2011, by the Japanese Patent Office in corresponding Japanese Patent Application No. 2009-520702.

APPARATUS AND METHOD FOR FORMING AIR-LAID ABSORBENT CORES

TECHNICAL FIELD

The present disclosure relates to an apparatus for forming air-laid absorbent cores, comprising a first and second mat-forming wheel, each of the mat-forming wheels having at least one mould along its peripheral surface, air-laying means and for supplying air-entrained fibrous material to the moulds on each mat-forming wheel, suction means maintaining the formed core elements in the respective moulds during a part of the path of the moulds on the respective mat-forming wheel and means for superposing a core element on the first mat-forming wheel and a core element on the second mat-forming wheel to each other, and a method using such an apparatus.

BACKGROUND

Apparatuses of the kind referred to above are used to produce multi-layered absorbent cores, at least one of the layers containing discrete particles of a highly absorbent material, preferably a so called superabsorbent material (SAP), which can absorb liquid in an amount several times it own weight. The fibres in the layers are preferably cellulosic and produced by defibration of pulp. Additionally, other types of fibres can be added. The fibres in the different layers can be the same or different.

Apparatuses according to the present disclosure are to be disposed in a manufacturing line for producing absorbent articles, such as disposable diapers, sanitary napkins, incontinence protectors and the like sanitary articles. It is therefore important that such apparatuses do not occupy a lot of space, especially in the length direction of such a production line. Nowadays, the production rate of such a production rate is high, approximately 600 cores per minute, and the present disclosure aims to allow even higher production rates. In such high speeds the centrifugal forces acting on the discrete particles in formed core elements are quite high and there is a problem of preventing these particles from falling out of such core elements. Apart from the cost consequence of losing relative expensive particle material, there is a risk that the lost particles will fall on components or equipment in the production line an adversely influence the functions thereof and also the environment. Lost particles must therefore somehow be taken care of. There is therefore a need to keep such losses of particles as low as possible.

Another problem is to ensure that the core elements formed on the respective mat-forming wheel of an apparatus of the kind described in the introduction are superposed on each other in the desired mutual relationship. If, for example, the leading edges of the superposed core elements are to be aligned with each other, a misalignment will visually be very apparent and will also adversely influence the function of the produced article. For example, if the produced article contains openings or the like in the superposed cores which should coincide or have a determined relationship relative each other in the superposed position of the core elements, a misalignment of those openings will have a detrimental effect on the functioning of the produced article.

A further problem with an apparatus according to the introduction is that there is a risk that the discrete particles air-laid onto a mould will damage the mould or obstruct or clog some of the openings in the mould. Such obstructions or clogging leads to an uneven distribution of air-laid material in the mould and will consequently adversely affect the absorptive properties of the produced article.

In EP-B1-O 958 801 is shown an apparatus, in which a web of tissue is wound on a mat-forming wheel and drawn against the walls of the moulds on the peripheral surface of the wheel. Thereafter, a layer of discrete particles is air-laid in the mould and air-entrained fibres are drawn into this layer of discrete particles to mix with the discrete particles. In FIG. 3 of this document, such an apparatus having two mat-forming wheels is disclosed. The air-laid bodies are delivered from each mat-forming wheel attached to the webs of tissue and the two webs of tissue together with the attached bodies are then superposed on each other. The bodies attached to the webs travel a rather long distance without suction means influencing the bodies thereon and there is a great risk that particles will fall out of the bodies during this travel. Moreover, with such a construction it seems hard to obtain a great accuracy of the relative positions of the bodies attached to the webs when superposed to each other.

In EP-B1-I 082 081 an apparatus according to the preamble of claim 1 is disclosed. In such an apparatus, only fibrous material is air-laid in the moulds on the first mat-forming wheel for forming a body on which a second body composed of a mixture of fibrous material and discrete particles of SAP is transferred from the second mat-forming wheel while the first body is still in its mould. A third layer of fibrous material is then air-laid over the composite of the first two bodies. During the transfer of the second body onto the first body, a part of the second body is always in the free air exposing both its sides thereto. There is thus a great risk that SAP-particles will fall out of these exposed parts of the second body, especially if the concentration thereof is high and the speed of the mat-forming wheels are high. After transfer of the second body onto the first body, the third layer air-laid thereon will prevent the SAP-particles in the second body from falling out. Although the accuracy of the positions of the superposed bodies is improved due to the first body being maintained in its mould during the transfer of the second body thereon, the second body has to move in free air before being superposed onto the first body, a fact that reduces accuracy. Moreover, in the second mat-forming wheel there are no means for preventing discrete particles air-laid in the moulds to obstruct or clog the openings in the bottoms of these moulds.

Sanitary absorbent articles, such as diapers, are often provided in different sizes. When such different sizes of cores for the "same" absorbent article are to be produced on the same apparatus, like the apparatus described in the introduction, the moulds on the mat-forming wheels have to be changed. This is a time-consuming operation, which also involve storage of the different moulds not used for the size in question and which reduce the cost-efficiency of the manufacturing process, especially for small product series.

For such articles it is also advantageous to have core elements with a high amount of SAP-particles (more than 50%) mixed into the fibrous material. A problem with having such an high amount SAP-particles in a core element is that the strength of the core element is reduced. The risk for losses of SAP-particles during forming and transport of such elements is of course increased.

Due to the above mentioned risks for loss of SAP-particles and the risk for formed cores to be damaged during transport and handling due to the reduced strength of core element with high content of SAP-particles, equipment for forming such cores, such as mat-forming wheels, are disposed within a line for the manufacturing of sanitary article so that the transport of core element formed on the wheels between forming and further treatment of the core is very short. Since mat-forming wheels are large components it would be advantageous if these components could be located at a distance from other components in the manufacturing line so that available space can be used as efficient as possible.

OBJECTS AND SUMMARY

It is an objective of the present disclosure to in an apparatus according to the introduction improve the accuracy of the transfer of a core element onto another, prevent air-laid discrete particles from damaging and/or clogging the moulds and prevent excessive losses of discrete particles from formed core elements. Moreover, it is an objective of the present disclosure to reduce the need for changing moulds when different sizes of the same product are to be produced. It is also an objective of the present disclosure to enable use of high SAP-particle concentration in core elements and to strengthen the formed cores so that these are transportable without risk for loss of SAP-particles or damage due to the transport. It is also an objective of the present disclosure to accomplish this without significantly increase the space required for the apparatus in a production line for the manufacturing of sanitary absorbent articles.

These objectives are accomplished by an apparatus for forming air-laid absorbent cores, comprising a first and second mat-forming wheel, each of the mat-forming wheels having at least one mould along their peripheral surface, air-laying means for supplying air-entrained fibrous material to the moulds on each mat-forming wheel, suction means maintaining the formed core elements in the respective moulds during a part of the path of the moulds on the respective mat-forming wheel and means for superposing a core element on the first mat-forming wheel and a core element on the second mat-forming wheel to each other, characterized by means for applying a first and second web of casing material onto the peripheral surface of the first and second mat-forming wheel, respectively, whereby suction means inside the respective mat-forming wheel will draw the material in the web to abutment against the bottom of a mould passing said suction means, means for providing a third web of casing material provided with a bonding agent on at least one side thereof into the nip between the first and second mat-forming wheel, means providing an adhesive coating on at least one side of the third web, the mat-forming wheels being so positioned that the formed core elements on the respective first and second mat-forming wheels will abut the third web when passing the nip between the first and second mat-forming wheel, whereby the air-laid core elements will be at least partly encapsulated in casing material.

In a preferred embodiment, means are provided for pressing together the portions of the three webs located outside the contour of the core element, containing the first and second core element, after having passed the nip.

Means can be provided for passing the unit having or consisting of the superposed first and second core elements, the intermediate third web and the first and second web through a pair of rollers after having passed the nip between the first and second mat-forming wheel. Said rollers are preferably profiled and located in the area between the first and second mat-forming wheel near the nip between the wheels.

In an alternative, means are provided for transferring one of the first and second web from one of the first and second mat-forming wheels to the other after passage of the nip between said wheels and means are provided for transferring the unit having or consisting of the three webs and the superposed core elements transported together on the first or second mat-forming wheel to a compressing device.

At least the air-laying means associated with the second mat-forming wheel can comprise means for supplying a mixture of air-entrained fibrous material and discrete particles.

The moulds of the mat-forming wheels can have different sizes, at least in the circumferential direction of the mat-forming wheels, and the moulds on the first mat-forming wheel can be larger than the moulds on the second mat-forming wheel.

The disclosure also relates to a method of forming air-laid absorbent cores, comprising the steps of: forming first and second core elements by air-laying of air-entrained fibrous material to moulds on a first and second mat-forming wheel, each of said mat-forming wheels having at least one mould along their peripheral surface, superposing a core element on the first mat-forming wheel and a core element on the second mat-forming wheel onto each other, characterized by applying a first and second web of casing material to the peripheral surface of the first and second mat-forming wheel, respectively, before air-laying of a mixture of air-entrained fibrous material and optionally discrete particles in the mould, passing a third web of casing material coated on at least one side with an adhesive coating through the nip between the first and second mat-forming wheels, positioning the mat-forming wheels so that the formed core elements on the respective first and second mat-forming wheels will abut the third web when passing the nip between the first and second mat-forming wheel, whereby the air-laid core elements will be at least partly encapsulated in casing material.

In a preferred embodiment, wherein means are provided for pressing together the portions of the three webs located outside the contour of the core element, containing the first and second core element. In one alternative, means are provided for passing the unit having or consisting of the superposed first and second core elements, the intermediate third web and the first and second web through a pair of rollers after having passed the nip between the first and second mat-forming wheel, whereby the core elements are drawn out of its respective mould immediately after having passed the nip. Advantageously profiled rollers are provided and located in the area between the first and second mat-forming wheel near the nip between the wheels.

In another alternative, one of the first and second web from one of the first and second mat-forming wheels is transferred to the other after passage of the nip between said wheels and the unit having or consisting of the three webs and the superposed core elements transported together on the first or second mat-forming wheel is transferred to a compressing device.

The moulds of the mat-forming wheels can be given different sizes, at least in the circumferential direction of the mat-forming wheels, and the moulds on the first mat-forming wheel can be given a larger size than the moulds on the second mat-forming wheel. A mixture of air-entrained fibrous material and discrete particles can be supplied to the moulds of both the first and second mat-forming wheel and nonwoven is preferably chosen as material for the three webs of casing material.

BRIEF DESCRIPTION OF THE DRAWINGS

The disclosure will now be described with reference to the enclosed Figures, which are for the purpose of illustration of various non-limiting embodiments of the disclosure, of which.

DESCRIPTION OF EMBODIMENTS

Figure 1:
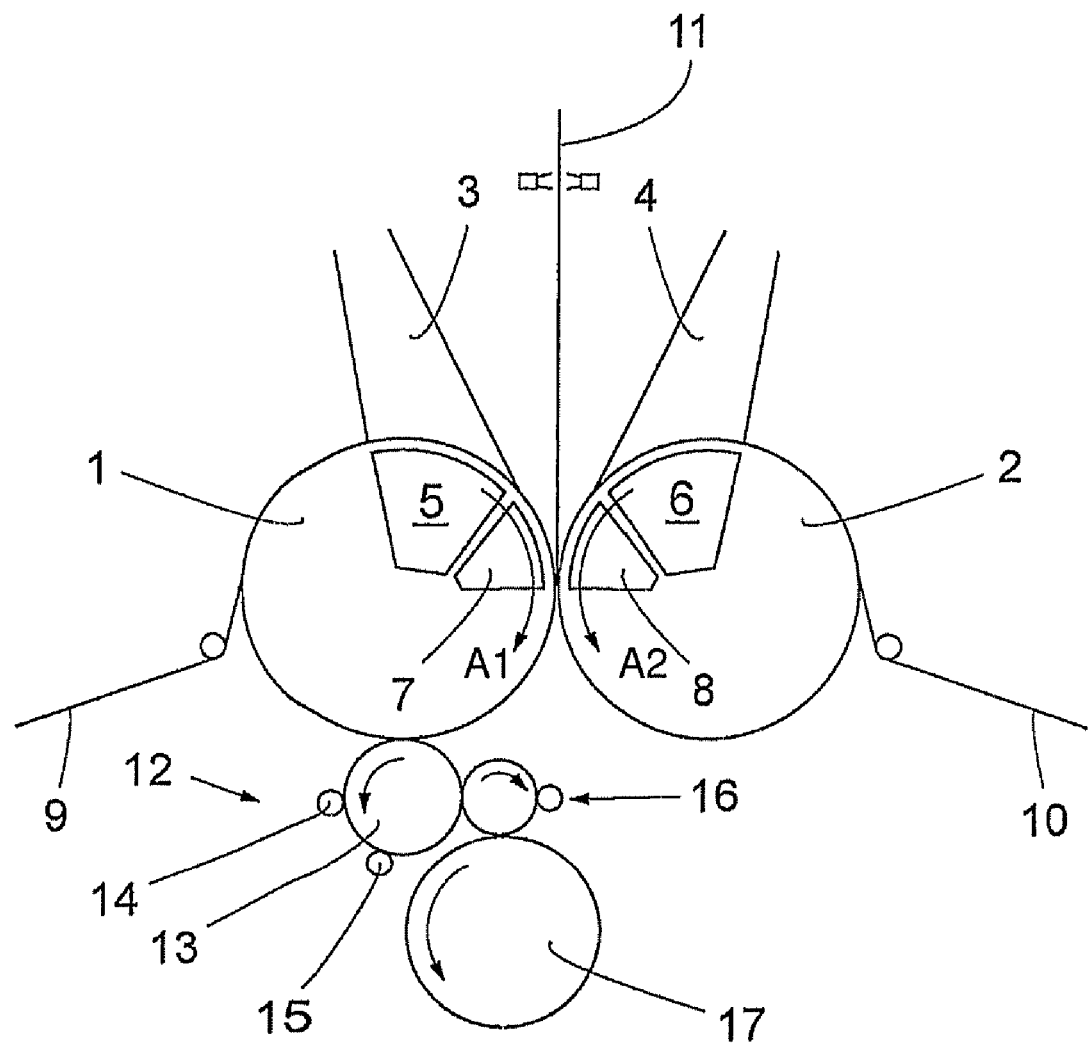
FIG. 1 schematically shows a side view of an apparatus for forming air-laid absorbent cores according to a preferred embodiment of the disclosure, and FIG. 2 schematically shows a view similar to FIG. 1 of a second embodiment.

In FIG. 1, a first preferred embodiment of an apparatus for forming air-laid absorbent cores is schematically disclosed. The apparatus includes two formation drums or mat-forming wheels, a first wheel 1 and a second wheel 2, each having a series of moulds on their peripheral surfaces. The mould bottom or screen can be made of wire mesh or perforated steel sheet. Associated to the peripheral surfaces of the two mat-forming wheels 1,2 is a formation chamber or hood 3,4. Opposite the hood 3 of the first mat-forming wheel, a suction box 5 is disposed inside the wheel 1 in order to drawn air-entrained pulp or a mixture of pulp and SAP-particles into a mould passing between hood 3 and box 5. Similarly, a suction box 6 cooperating with hood 4 of the second mat-forming wheel 2 is disposed inside wheel 2. The apparatus also comprises a mill, for example a hammer mill, for defibration of pulp, pipes used for fibre or fibre/SAP transport, and a fan for the transport of fibre or fibre/SAP to the respective hood 3,4. These components are conventional and well know to one skilled in the art and will not be further described. For the understanding of the present disclosure it is enough to say that a homogenous mixture of air fibres and possible SAP-particles may be present in the hoods when the apparatus is in use. As stated above, each hood 3,4 is cooperating with a separate suction box 5,6, respectively, which is stationary and located in the interior of the respective mat-forming wheel. When the moulds on the peripheral surface of each wheel pass between a hood and its associated suction box during the rotation of the wheel, the air-entrained material in the hood will be drawn into the mould and deposited therein. In the mat-forming wheels 1,2, suction boxes 7 and 8, respectively, are present for maintaining the core elements formed in the moulds in the their respective mould and for maintaining the shape of the formed core elements.

A web 9,10 of casing material, for example nonwoven, is applied to the peripheral surface of each mat-forming wheel 1,2 upstream of the respective hood 3,4, as seen in the rotational direction of the respective mat-forming wheel 1,2, as illustrated by arrows A1,A2. When such a web passes over the respective suction box 5,6, the suction forces will draw the web into the mould into abutment with the bottom thereof.

The mat-forming wheels 1,2 are disposed side-by-side, the nip between them being dimensioned to be at least 6 mm. The term "nip" denotes the point at which the peripheries of the wheels 1,2 are closest to each other.

A third web 11 of casing material is made to run through the nip between the wheels 1,2. This web is by suitable means, for example the glue applicators, schematically indicated in FIG. 1, coated with an adhesive coating on one or both sides. The adhesive is preferable sprayed onto the web over its whole surface so that less than 10% of the area of the web is covered.

It is of course also possible to apply a bonding agent in other ways, for example, the web can be pre-coated with an adhesive which is activated by water or an adhesive which is non-tacky at room temperature and activated by heat.

In the apparatus according to FIG. 1, the second core element formed on the second mat-forming wheel 2 is transferred together with the second web 10 onto the first core element formed on the first mat-forming wheel 1 and held thereon by this web, as will be described in detail below, until the composite core comprising the superposed first and second core elements is delivered to a compression device 12 having or consisting of two rollers 14,15 cooperating with a transfer roller 13.

After compression, the composite core passes through a cutting device 16 and is then transferred to an accelerator device 17 before it is delivered into the line for manufacturing of absorbent articles of which the apparatus according to the disclosure is a part.

A method of using the apparatus illustrated in FIG. 1 will now be described.

As the mat-forming wheels 1 rotates in the direction of arrows A1, the moulds therein successively passes between the hood 3 and the suction box 5. The hood 3 preferably delivers a mixture of pulp fibres and SAP-particles which is drawn into the moulds on the first mat-forming wheel by the suction forces and deposited in therein. A first core element is thus formed in said moulds. As the mat-forming wheel 2 rotates in the direction A2, the moulds therein successively pass between hood 4 and suction box 6. During this passage a mixture of pulp fibres and SAP-particles is air-laid in the moulds in the second wheel 2. The layer of pulp and SAP-particles has a thickness of 5 mm. The concentration of SAP-particles in this layer is higher, about 50-70 wt %, than in the first core elements air-laid in mat-forming wheel 1, in which the concentration of SAP-particles is about 10-30 wt %. The layers of nonwoven 9,10 nearest the bottoms of the moulds in the first and second wheel have the functions of preventing SAP-particles from obstructing and clogging the holes in the mould bottom, thereby causing an uneven distribution of air resulting in an uneven distribution of air-laid material, and from damaging the these bottom. It has surprisingly been shown that SAP-particles in a mixture of pulp fibres and SAP-particles can wear out the material in the mould bottoms. These webs also have the function of preventing SAP-particles from falling out of the core element formed in the respective mould after the first and second core elements are drawn out of their moulds, during transfer of the composite core from wheel 1 to the compression device 12.

The moulds in the wheels 1,2 are shallower than the core elements formed therein. After the core elements have been formed by air-laying in the respective moulds, the core elements are maintained in their respective mould by suction boxes 7, 8 until they reach the nip between the mat-forming wheels 1,2.

The nip is preferably dimensioned so that the outsides of the core elements, i.e. the sides thereof distal from the respective mould bottom, abut each other in the nip. In other words, the nip constitutes a "marrying point" for the two core elements in which they get together. The nip is preferably dimensioned so that normally the parts of the core elements overlapping each other are slightly compressed in the marrying point. The suction boxes 7,8 on the respective mat-forming wheel 1,2 end at the marrying point. At the nip, the web 10 leaves the mat-forming wheel 2 and is applied to the peripheral surface of mat-forming wheel 1 on top of the core elements traveling on this surface. As the web 10 leaves the moulds on mat-forming wheel 2 it also draws the core element formed in the mould with it and thereby supports this core element during transfer from mat-forming wheel 2 to mat-forming wheel 1. Due to the arrangement of the nip and the "overfilling" of moulds, all the overlapping points of a core element on one of the wheels 1,2 will in the nip come to abutment with the outside of core element on the other wheel while it still is maintained in its mould and is not until then superposed a core element on the other wheel. Thus an extremely controlled and accurate superposing of core elements is accomplished.

Due to its high content of SAP-particles, there is a risk that the strength of the core elements formed in the moulds in the second mat-forming wheel 2 is not high enough for ensuring integrity thereof during continued transport and handling. However, in the apparatus described referring to FIG. 1, the core elements on the second mat-forming wheel is reinforced by being adhesively attached to the third web 11 in the nip between wheels 1,2. As is evident from FIG. 1, this web is passing intermediate of the core elements on the respective wheel and will therefore be adhesively attached to both of these core elements as these are pressed to abut each other in the nip. The composite core leaving the nip has thus two superposed core elements which both are wholly encapsulated between two layers of casing material, namely the three webs 9,10,11, whereby the intermediate third layer 11 is common for both of the core elements. Thus, both of the core elements making up the core are reinforced.

After the core element on the second mat-forming wheel 2 has been transferred to wheel 1 onto the core element on the first wheel 1 together with webs 10,11, these web 10,11 will also prevent SAP-particles from falling out of this core element during transport.

The composite core comprised of the two superposed core elements, the two outer webs 9,10 and the intermediate web 11 is thereafter transported on peripheral surface of the wheel 1 and then transferred to a transferring roller 13 functioning as anvil for two compression rollers 14,15 providing a two-step compressing of said composite core. The compressed core is then passing a rotating cutting device 16 in which individual cores are cut from the composite unit having or consisting of a row of composite cores held together by the three webs 9,10,11 and the individual core are transferred to an accelerator 17 which delivers the individual cores to other components in the line for manufacturing of disposable sanitary absorbent articles, for example delivers the cores on a web of liquid impermeable material constituting one of the outer casing sheets of such an article.

As stated above, the superposed core elements leaving the nip between the mat-forming wheels 1,2 are each encapsulated by two webs of nonwoven material, webs 9,11 and 10,11, respectively. This means that a core element on one of the wheels 1,2 need not have its leading part supported by a part of the core element on the other wheel, it is enough that the leading part is supported between said two webs which in turn are positively guide during the transfer of on core element on one wheel to the peripheral surface of the other wheel.

By the apparatus described above it is thus possible to produce a core having or consisting of two core elements in an accurate overlapping superposed relationship to each other. It is of course also possible to produce a core in which the superposed core elements do not overlap each other. Such an apparatus makes it possible to produce cores having different sizes by varying the overlapping between the core elements.

Such an apparatus must of course have means for controlling the produced overlap between the core elements, i.e. means for changing the synchronization of the mat-forming wheels in order to control the time at which the leading edge of a mould on one of the mat-forming wheels passes the nip in relation to when the leading edge of a mould on the other mat-forming wheel passes the nip. An easy way of controlling the overlap is to vary the start of rotation of the mat-forming wheels so that one of the mat-forming wheels starts its rotation before the other. Another way is of course to manually set an angular displacement of one wheel in relation to the other.

An apparatus according to the embodiment shown enables a production of absorbent cores at a very high rate of even more than 600 cores per minute.

Figure 2:
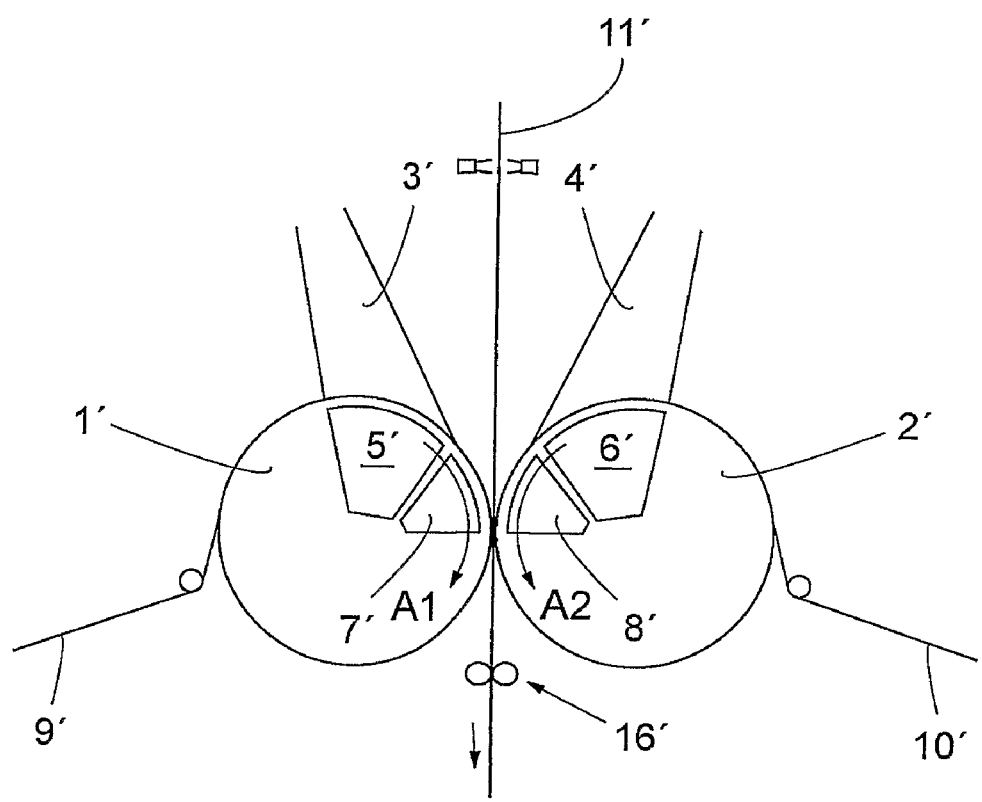

In FIG. 2, a second embodiment of the apparatus is schematically shown.

This embodiment differs from the embodiment described with reference to FIG. 1 mainly in that the superposed core elements are drawn out of their respective mould directly after having passed the nip between the two mat-forming wheels. Components in the apparatus in the second embodiment similar to components in the apparatus in FIG. 1 are given the same reference numerals with the addition of a prime sign.

As is evident from FIG. 2, a pair of rollers 16' is present between the mat-forming wheels 1',2' immediately below the nip between these two wheels. The webs 9',10',11' and the row of superposed core elements held between the webs 9',10' and attached to the intermediate web 11' pass through this pair of rollers 16'. The pair of rollers 16' functions to positively attach the parts of the webs 9',10',11' extending outside the contour of the superposed core elements together by pressing the webs 9',10' against the adhesive coating on the opposite sides of web 11'. The rollers can be profiled in order not to compress the core elements before the encapsulation provided by the webs is tightly sealed by the adhesive attachment of the webs to each other. A row of successive composite core being wholly and tightly encapsulated, wherein the row of composite cores is held together by intermediate web material, is thus created. By such an arrangement the composite cores can be transported as desired without risk for damage of the core elements or risk for SAP-particles to fall out. An apparatus according to the second embodiment can thus be located anywhere in the line for the manufacturing of sanitary absorbent articles an enables available space in such a line to be optimally used.

The method of forming composite cores with core elements having a high content of SAP-particles according to the present disclosure and the apparatus used offers a lot a advantages in relation to known methods and apparatuses. By having a wholly encapsulate composite core leaving the nip between the two mat-forming wheels, the risk for loss of SAP-particles is greatly reduced. The webs used for encapsulation and transport of the formed composite cores is also used for drawing the cores out of the respective mould making blowing devices commonly used for this purpose obsolete and the webs applied to the bottoms of the moulds also protect the moulds from clogging and damage. The intermediate web reinforces the core elements and reduces the risk for leak-through of adhesive during compression since the adhesive is not directly coated onto one of the outer webs but to the intermediate web. Such a leak-through will adversely affect the function of the compressing device. As is evident from the second embodiment, the pair of mat-forming wheels can be located anywhere in relation to other components in the line for the manufacturing of sanitary absorbent articles.

The apparatuses according to the described embodiments can of course be modified in several respects without leaving the scope of disclosure. The dimensions of the core elements can be different than described. Other types of casing material than nonwoven can be used and the core element on the first mat-forming wheel need not contain SAP-particles. More than one air-laying device can be associated with each mat-forming wheel. Different fibres can be used in the different air-laying devices and the cutting device and accelerator for delivering produced cores to the production line for the manufacturing of absorbent articles can be any type of such equipment used in such production line. The disclosure shall therefore only be limited of the wording of the issued claims.

The invention claimed is:

1. An apparatus for forming air-laid absorbent cores, the apparatus comprising:
   first and second mat- forming wheels, each of the mat-forming wheels having at least one mould along its peripheral surface,
   air-laying means for supplying air-entrained fibrous material to the moulds on each mat-forming wheel,
   suction means for maintaining the formed core elements in the respective moulds during a part of the path of the moulds on the respective mat-forming wheel, and
   means for superposing a core element on the first mat-forming wheel and a core element on the second mat-forming wheel to each other,
   the apparatus further comprising:
   means for applying first and second sheets of casing material onto the peripheral surface of the first and second mat-forming wheels, respectively, whereby suction means inside the respective mat- forming wheel will draw the material in the sheet to abutment against the bottom of a mould passing said suction means,
   means for providing a third sheet of casing material provided with a bonding agent on at least one side thereof into a nip between the first and second mat-forming wheels, and
   means for providing an adhesive coating on at least one side of the third sheet,
   wherein the mat-forming wheels are positioned so that the formed core elements on the respective first and second mat-forming wheels will abut the third sheet when passing the nip between the first and second mat-forming wheels, whereby the air-laid core elements will be at least partly encapsulated in casing material.

2. The apparatus according to claim 1, further comprising means for pressing together portions of the three sheets located outside the contour of the core element, containing the first and second core elements, after having passed the nip.

3. The apparatus according to claim 2, wherein the means for pressing together comprise a means for passing a unit comprising the superposed first and second core elements, the intermediate third sheet and the first and second sheets through a pair of rollers after having passed the nip between the first and second mat-forming wheels.

4. The apparatus according to claim 3, wherein said rollers are profiled and located in the area between the first and second mat-forming wheels near the nip between the wheels.

5. The apparatus according to claim 2, wherein the means for pressing together comprise a means for transferring one of the first and second sheets from one of the first and second mat-forming wheels to the other after passage of the nip between said wheels.

6. The apparatus according to claim 5, wherein the means for pressing together comprise a means for transferring the unit consisting of the three sheets and the superposed core elements transported together on the first or second mat-forming wheel to a compressing device.

7. The apparatus according to claim 1, wherein at least the air-laying means associated with the second mat-forming wheel comprises means for supplying a mixture of air-entrained fibrous material and discrete particles.

8. The apparatus according to claim 1, wherein the moulds of the mat-forming wheels have different sizes, at least in the circumferential direction of the mat-forming wheels, and the moulds on the first mat-forming wheel are larger than the moulds on the second mat-forming wheel.

9. A method of forming air-laid absorbent cores, the method comprising the steps of:
   forming first and second core elements by air-laying of air-entrained fibrous material to moulds on first and second mat-forming wheels, each of said mat-forming wheels having at least one mould along its peripheral surface, and
   superposing a core element on the first mat-forming wheel and a core element on the second mat-forming wheel onto each other,
   the method further comprising:
   applying first and second sheets of casing material to the peripheral surface of the first and second mat-forming wheels, respectively, before air-laying of a mixture of air-entrained fibrous material and discrete particles in the mould,
   passing a third sheet of casing material coated on at least one side with adhesive coating through a nip between the first and second mat-forming wheels, and
   positioning the mat-forming wheels so that the formed core elements on the respective first and second mat-forming wheels will abut the third sheet when passing the nip between the first and second mat-forming wheels, whereby the air-laid core elements will be at least partly encapsulated in casing material.

10. The method according to claim 9, the method further comprising pressing together portions of the three sheets located outside the contour of the core element and containing the first and second core elements.

11. The method according to claim 10, wherein the pressing together step comprises passing a unit comprising the superposed first and second core elements, the intermediate third sheet and the first and second sheets through a pair of rollers after having passed the nip between the first and second mat-forming wheels, whereby each core element is drawn out of its respective mould immediately after having passed the nip.

12. The method according to claim 11, wherein the rollers are located in the area between the first and second mat-forming wheels near the nip between the wheels.

13. The method according to claim 10, the method further comprising transferring one of the first and second sheets from one of the first and second mat-forming wheels to the other after passage of the nip between said wheels.

14. The method according to claim 13, the method further comprising transferring a unit comprising the three sheets and the superposed core elements transported together on the first or second mat-forming wheel to a compressing device.

15. The method according to claim 9, wherein the moulds of the mat-forming wheels have different sizes, at least in the circumferential direction of the mat-forming wheels, and the moulds on the first mat-forming wheel have a larger size than the moulds on the second mat-forming wheel.

16. The method according to claim 9, wherein a mixture of air-entrained fibrous material and discrete particles is supplied to the moulds of both the first and second mat-forming wheels and nonwoven is chosen as material for the three sheets of casing material.

* * * * *